United States Patent [19]

Lukens, Jr.

[11] 4,248,854
[45] Feb. 3, 1981

[54] PRODUCTION OF ANTIBODY TOWARD ASBESTOS AND IMMUNOASSAY THEREWITH

[75] Inventor: Herbert R. Lukens, Jr., La Jolla, Calif.

[73] Assignee: The United States of America as represented by the Secretary of the Navy, Washington, D.C.

[21] Appl. No.: 70,073

[22] Filed: Aug. 27, 1979

[51] Int. Cl.³ .................. G01N 33/54; G01N 33/58; G01N 33/84
[52] U.S. Cl. .................................. 424/8; 23/230 B; 250/302; 424/1; 424/7; 424/12
[58] Field of Search .................. 424/1, 3, 7, 8, 11, 424/12, 13, 155, 357; 23/230 B; 250/302

[56] References Cited

PUBLICATIONS

Lukens et al., Biol. Abs., vol. 64, 1977, Ab. No. 5278.
Lukens, Biol. Abs., vol. 67, 1979, Ab. No. 51441.
Kagan, Chem. Abs., vol. 87, 1977, Ab. No. 87: 79383e.
Williams, Methods in Immunol & Immunochem., Acd. Press, N.Y., vol. V, 1976, pp. 424–437.

*Primary Examiner*—Anna P. Fagelson
*Attorney, Agent, or Firm*—R. S. Sciascia; A. L. Branning; J. C. LaPrade

[57] ABSTRACT

The invention provides a reaction product of chrysotile asbestos with an antigenic serum protein, preferably albumin, that has particular utility as an antigen in producing antibody to asbestos. The reaction product of asbestos with an antigenic serum protein also can be used in a method for producing an antibody toward asbestos by immunizing a laboratory animal with the reaction product, of asbestos and a serum protein, allowing it to remain in the blood of the animal for a sufficient period of time and thereafter recovering antibody globulins from the laboratory animal.

20 Claims, No Drawings

PRODUCTION OF ANTIBODY TOWARD ASBESTOS AND IMMUNOASSAY THEREWITH

BACKGROUND OF THE INVENTION

Asbestos is a generic term describing a variety of naturally formed hydrated silicates that, upon mechanical processing, separate into mineral fibers. There are two fundamental varieties of asbestos: serpentine and the amphiboles. Serpentine asbestos is known as chrysotile and the amphiboles include five species identified as anthophyllite, amosite, crocidolite, actinolite, and tremolite. Each of these varieties of asbestos differ from each other chemically.

Asbestos fibers are unique minerals combining unusual physical and chemical properties which make them useful in the manufacture of a wide variety of residential and industrial products. Of mineral origin, asbestos does not burn, does not rot, and, dependent on variety, possesses extremely high tensile strength as well as resistance to acids, bases, and heat. Similarly, when processed into long, thin fibers, asbestos is sufficiently soft and flexible to be woven into fire-resistant fabrics.

Historical records show that asbestos has been known for more than 2000 years. Applications of this noncombustible fiber are mentioned by Plutarch and Pliny, particularly with reference to asbestos textiles used for cremation cloths, oil lamp wicks, etc.

The asbestos industry per se had its inception in the 18th century in the Russian Ural mountains and by the mid-19th century both Italian chrysotile and tremolite varieties were mined and processed into commercial products. At the same time asbestos was discovered and mined on a commercial scale at Thetford Asbestos in Quebec, Canada. To this day, these Canadian and Russian locations are the major producers of chrysotile asbestos.

ORIGIN AND OCCURRANCE

Through the years, the origin of asbestos has been the subject of extensive geological research. Serpentine asbestos occurs under widely differing geological conditions from the amphiboles. Similarly, the modes of occurrence or the manner in which the fibers are physically imbedded in the host rock also differ widely. The current opinion is that chrysotile fiber resulted from two separate metamorphic reactions in ultrabasic rocks of igneous origin. The initial hydrothermal reaction altered the olivines and pyroxenes to serpentine. At a subsequent point the serpentine was redissolved and the mineral-rich solutions flowed into cracks and crevices in the host rock where chrysotile fiber was reprecipitated.

In this reprecipitation process, asbestos fiber was usually deposited in a cross-vein mode of occurrence; i.e., the fiber is arranged perpendicular to the wall rock.

CHRYSOTILE ASBESTOS

Crystal Structure. The mineral species associated with the serpentine group, serpentine, chrysotile, lizardite, and antigorite, although differing structurally, are compositionally almost identical. All have the approximate chemical composition of $Mg_3(Si_2O_5)(OH)_4$. The crystal structure of chrysotile is layered or sheeted similarly to the kaolinite group. It is based on an infinite silica sheet $(Si_2O_5)_n$ in which all the silica tetrahedra point one way. On one side of the sheet structure, and joining the silica tetrahedra, is a layer of brucite, $Mg(OH)_2$, in which two out of every three hydroxyls are replaced by oxygens at the apices of the tetrahedra.

Mismatches and strains between the layers cause the structure to curve and form cylinders or fibers. Individual chrysotile fibers have ultimate diameters of 0.02-0.03 $\mu$m. X-ray and electron microscope studies have confirmed this cylindrical form and diameter range. In fact, the first electron microphotographs indicated a tubular structure. This characteristic appearance has now become one of the more definitive identification techniques for chrysotile.

Electron microphotographs have shown most chrysotile fibers with a hollow cylindrical form and a single magnesia-silica sheet rather than the earlier double-layer concept. The lattice planes have a multispiral arrangement as suggested by earlier x-ray studies.

Chemical and Surface Properties. Chrysotile asbestos is a naturally formed mineral. The chemical compositions vary somewhat, depending on deposit location, from the idealized composition of $Mg_3(Si_2O_5)(OH)_4$. Chemical analyses of chrysotile range approximately as follows: $SiO_2$, 37-44%, MgO, 39-44%; FeO, 0-6.0%; $F_2O_3$, 0.1-5%; $Al_2O_3$, 0.2-1.5%; CaO, trace-5.0%; $H_2O$, 12.0-15.0%. Variations in chemical analyses may be due to either associated mineral impurities or to isomorphic substitutions in the crystals lattice. Common mineral impurities found in commercial grades of chrysotile from various locations include magnetite, chromite, brucite, calcite, dolomite, and awaruite. Within the chrysotile lattice, nickel and iron can occur as minor isomorphic substitutions for magnesium. Chrysotile, a hydrated silicate, is subject to thermal decomposition at elevated temperatures. This thermal decomposition is a twostage reaction consisting first of a dehydroxylation phase and then a structure phase change. Dehydroxylation or the loss of water occurs at 600°-780° C. at 800°-850° C. the anhydride breaks down to forsterite and silica. These reactions are irreversible and are illustrated by the typical differential thermal analysis.

Structural changes in chrysotile can occur under conditions of intense grinding. As a result of these effects the structure can become amorphous and no longer identifiable by either x-ray diffraction or electron microscopy. These structural changes apparently occur because of localized temperature surges in the fibrils with accompanying dehydroxylation as they absorb the tremendous impact energies, e.g., extensive dry ball milling results in an amorphous mass and well ball milling results in short fibrils that retain their crystallinity.

Because of its hydroxyl outer layer, chrysotile is readily attacked by acid and will, ultimately, completely dissolve the magnesium component, leaving essentially a fibrous, but fragile, silica structure. Similarly, because of its alkaline surface, chrysotile is not readily attacked by caustic solutions except under conditions of extreme alkali concentration and elevated temperatures.

Dispersions of chrysotile fiber in carbon dioxide-free distilled water exhibit alkaline properties. Such suspensions will reach a pH of 10.33 as with magnesium hydroxide suspensions tested under the same conditions. Solubility product constants for chrysotile fibers range from $1.0 \times 10^{-11}$ to $3 \times 10^{-12}$, indicative of the magnesium hydroxide outer layer.

The electrokinetic behaviour of chrysotile is also related to its surface characteristics. Normally, below its isoelectric point of approximately pH 11–12, chrysotile exhibits a positive charge. Above this pH range, it demonstrates a negative charge. Exceptions to this general behavior has been noted with chrysotile fibers from certain location.

Because of its very small fiber diameter, its high specific surface area and its relatively reactive surface, chrysotile is a selectively adsorptive material. Commercial grades of chrysotile absorb as much as 2–3 wt % moisture from saturated air. Adsorption studides of a variety of organic copounds from both vapor and liquid media show that chrysotile has a greater affinity for polar molecules. Heats of adsorption have been measured ranging from 38 kJ/g (9 kcal/g) for hexane to 67 kJ/g (16kcal/g) for water (5,24–27). Chrysotile also adsorbs iodine from solutions in a manner similar to magnesium hydroxide or brucite. This adsorption characteristic is often used as a staining technique for the detection of chrysotile asbestos.

PHYSICAL PROPERTIES

Chrysotile asbestos is generally of serpentine structure, with cross and slip fiber veining. The essential composition is of hydrous silicates of magnesia. The crystal structure of chrysotile asbestos is fiberous and asbestiform and the crystal system is essentially monoclinic or pseudoorthorhombic. The hardness of chrysotile asbetos varies from 2.5 to 4.0 with a specific gravity of from 2.4 to 2.6. The refractive index varies from about 1.50 to about 1.55.

The crysolite asbestos is generally very flexible with fiber length of great variation with texture varying from soft to harsh. The specific heat of asbestos is approximately 1113 J/(Kg-K).

Asbestos fibers are used in composite materials (qv) to provide reinforcement. Tensile strength of the fiber is, therefore, an important and highly significant physical property. Unfortunately, because of their extremely fine diameter and the complicating factor of the effect of sample length on strength determinations, it is extremely difficult to measure the tensile strengths of asbestos with precision. Most recent information indicates typical chrysotiles have tensile strengths in the order of 3727 MPA($5.4 \times 10^5$ psi) which exceeds corresponding values for steel piano wire and fiber glass. A comparison of typical strength values for the different asbestos varieties is given in Table 3. Since all these measured values are far less than the theoretical value of over 10,000 MPA ($1.45 \times 10^6$ psi) attributable to silicate chain structures, the values given should be considered as relative for the different varieties rather than specific.

Physical strengths of asbestos are adversely affected by elevated temperatures.

What visually appears to be a single fiber in commercial grades of asbestos is in actuality a bundle of a large number of individual fibrils. These bundles can be subdivided into a multitude of finer bundles, but only with special processing can a large portion of fiber mass be divided to its ultimate fibril diameter. The specific surface areas of commercial asbestos fibers vary with the extent of mechanical defibrillation. Surface areas by nitrogen adsorption tests on samples teased by hand from chrysotile crude are 4–12 $m^2/g$; however, when aggressively milled or fiberized, surface areas of 30–50 $m^2/g$ result. Chrysotile asbestos can be separated into smaller diameter fibrils (higher specific area) more readily under wet processing conditions than under dry mechanical milling. For this reason many asbestos product manufacturing processes utilize wet opening techniques to provide improved fiber reinforcing efficiencies.

ENVIRONMENTAL HAZARDS OF ASBESTOS

Asbestos is a mineral in widespread use and has known carcinogenic properties. It occurs in nature and finds a multiplicity of uses in our heavily industrialized society. Its major applications are in the construction industry where it serves as a filler, reinforcer, insulator, coating agent, wear-resisting agent, etc. These uses consume many hundreds of tons of the mineral each year. During the course of mining, roadbuilding, tilling the soil, landslides, and weathering, natural formations containing asbestos are disturbed and these processes, as well as the industrial ones, give rise to environmental pollution by asbestos. Unfortunately, though, it is a material that cannot be detected nor quantatively measured quickly and easily at low concentrations. Consequently, monitoring tends to be carried out infrequently with resultant uncertainty in the true environmental hazard that it presents.

Among the recognized pathological consequences of significant asbestos uptake are asbestosis, pleural calcification, bronchogenic carcinoma, mesothelial tumors, and gastrointestinal malignancies. Gastrointestinal malignancies have been tied to asbestos in drinking water, while the other four are associated with the breathing in of small airborne particles of asbestos.

HEALTH AND SAFETY FACTORS

The inhalation of excessive quantities of free asbestos fibers over prolonged periods of time can increase the risk of developing certain diseases of the lung within a number of years. Three diseases associated with the inhalation of asbestos are: asbestosis, a nonmalignant fibrotic lung condition; bronchogenic (lung) carcinoma; and mesothelioma, a rare cancer of the lining of the chest or abdominal cavities.

Reduction of asbestos dust exposure is at present the only known method of preventing disease among asbestos industry workmen. When dust levels are low, risk to employees and the incidence of asbestos-related disease drop sharply. Cigarette smoking greatly increases the risk of developing bronchogenic cancer among persons encountering heavy asbestos exposure. Nonsmoking asbestos workers show no greater incidence of bronchogenic cancer than the average nonsmoker.

MEASUREMENT AND SAMPLING TECHNIQUES OF THE PRIOR ART

The sampling and measurement techniques for the determination of asbestos in air and water are similar. The currently preferred method for measuring the mineral in air calls for passing the air through a very fine-pore filter that can be rendered transparent with a suitable organic liquid so that the specimen can be examined by light microscopy under phase contrast illumination. The examination can detect $>0.2$-$\mu$m-diameter fibers and relies upon morphology to indicate asbestos. Confidence in the results can be enhanced by modifications that indicate the refractive index of the fibers, provided they are $>1$ $\mu$m thick. Since the average diameter of chrysotile fibrils is about 30-fold smaller than this, however, it is obvious that light microscopy is not sensitive enough and is not a useful procedure unless the size distribution of asbestos at the sampling location is known.

An electron microscope equipped with nondispersive x-ray fluorescence apparatus will provide reliable determinations of both morphology and chemical composition. Infrared spectroscopy has been used to estimate chrysotile (the major form of asbestos), but this method does not differentiate chrysotile from other serpentine minerals. X-ray diffraction, which is more expensive, has been able to make this differentiation. However, to be effective, these two methods require tens of micrograms of asbestos in the collected sample.

None of the above methods are rapid or inexpensive, and only the most costly method—electron microscopy—is able to see very small-diameter fibers at low concentration. No reliable chemical method exists because there is no reagent that is able to differentiate between the various compounds of similar formula that include both asbestos and nonasbestos minerals. For example, morphology, as well as chemical composition, is needed to differentiate between antigorite (nonasbestos serpentine) and chrysotile (asbestos form of serpentine).

ANTIBODIES

Broadly speaking, an antibody is a substance formed in the body fluids of animals after an injection, it counteracts the affects of the injected substance, as antitoxins and precipitins.

The blood of all animals contains a variety of proteins which are capable of combining more or less specifically with, and inhibiting a number of known physiologically-active agents (if they were not active agents the odds are that such inhibitors would not be detected, and there may in fact be many more than have been recognized hitherto).

Antibodies (with the possible exception of natural antibodies) are characteristically formed as a specific response to the introduction into the tissues of the body of soluble materials which are recognized as foreign by the body. Their characteristic property is to combine, under physiological conditions, with the material in response to which they were formed.

ANTIGENS

One generic definition of an antigen is any material which causes the formation of antibodies upon injection.

The definition of what constitutes an antigen is inevitably circular, since it depends upon demonstrating that any particular material can elicit an immunological response specific for that material in some species of animal. In general the immunological response elicited is antibody production.

The first essential for a material to be antigenic is that it should contain chemical groupings which are not present in the substances which normally have access to the immunologically competent cells of the animal which is to be immunized. It is sufficient to state the well-known fact that animals do not as a rule make an immune response against constituents of their own bodies. For a chemical grouping to be foreign to an animal does not necessarily imply that it should contain entirely different building blocks—amino-acids, for example—but only that their arrangement should be such that at least part of the surface of the molecules presents a configuration which is unfamiliar to the organism. Since molecules have a three-dimensional structure it is easy to conceive that complex molecules such as proteins or polysaccharides, built up of many residues, will be folded so as to present surface arrangements which are peculiar to themselves. Alternatively, 'foreigness' can be a property which depends upon the presence in a molecule of chemical groups which are entirely unfamiliar to an organism such as when p-phenylarsonic response is determined by the foreign groups on the antigenic molecule.

A second essential is that the material should have a sufficiently great molecular weight. This statement is based on empirical observation rather than on any theoretical reasoning. It is easy to conceive that the larger a molecule is, the greater chance it will have of comprising unfamiliar antigenic determinant groups on its surface; also that large molecules are less readily lost from the body, e.g., by excretion in the urine (although smaller molecules may in fact be retained by becoming complexed with plasma proteins). Neither of these reasons, however, is sufficient to account adequately for the failure of molecules with molecular weight below about 5,000 to act as antigens. The smallest molecule to which an antibody response has been demonstrated is the pancreatic hormone glucagon (M.W. about 3,800).

PRIOR ART DETERMINATION OF ANTIGENS AND ANTIBODIES

The best method available to the clinical laboratory for determining amounts of antigens and antibodies in blood of humans and others is radioimmune assay (RIA), but the method has not found acceptance in the routine testing of blood for the presence of hepatitis associated antigens although serum hepatitis after blood transfusions is a serious and sometimes fatal complication of any medical procedures.

Radioimmune assay requires highly trained technicians capable of observing the precautions necessary in handling radioactive materials. The isotope-tagged reactants employed in RIA have a limited shelf life which makes their use costly. There is an urgent need for a simpler and less expensive method of determining extra-cellular antigens and/or antibodies in blood.

The prior art has also found that antigens and antibodies may be tagged with fluorescent materials, and that the amounts of the tagged antigens or antibodies can be determined by measuring the secondary light emission from the tagged antigens or antibodies when the same are exposed to brief pulses of very intense light.

The fluorescent tagging of antigens and antibodies is not new in itself. It was first described by A. H. Coons et al (Proc. Soc. Exp. Biol. & Med. 47, [1941] 200–202) and much information on the subject is found in the "Handbook of Experimental Immunology" (D. M. Weir ed., F. A. Davis Co., Philadelphia, Pa.) and in a paper on "Fluorescent Antibody Techniques" by W. B. Cherry (U.S. Dept. of HEW, 1960).

The known methods are limited to microscopic examination of intracellular antigens and to the fluorescent tagging of antibodies to a limited extent. When the known methods are scaled up to specimens useful in the clinical laboratory, the light necessary for producing fluorescence causes irreversible damage to the antigens and antibodies as well as decomposition (bleaching) of the fluorescent materials employed for tagging. The specimens and fluorescent material may some times deteriorate during the exposure to exciting light at such a high rate that the readings on the intensity of the secondary light emission cannot be correlated in a meaningful manner to the amounts of antigen or antibody originally present.

Therefore, after consideration of the difficulties of determining and measuring the quantitative presence of asbestos in a mammal or in the air or water it is a primary object of this invention to react asbestos with a blood serum protein for the purposes of forming a reagent useful in producing an antibody toward asbestos.

It is a further object of the invention to provide a reaction consisting of the conjugate a blood serum protein and asbestos.

It is also an object of this invention to provide a conjugate of an antigenic blood serum protein, such as albumin with the chrysotile type of asbestos.

It is another object of this invention to provide a method for producing an antibody toward asbestos by reacting chrysotile asbestos with a blood serum protein, immunizing an animal with the reaction conjugate and after sufficient time removing and isolating the antibody globulin to asbestos.

It is an additional object of the invention to provide several methods of determining the presence of asbestos in a sample.

SUMMARY OF THE INVENTION

This invention provides a basic method for production of antibodies to asbestos. Asbestos is reacted with an antigenic protein to produce an antigen. The antigen is subsequently used to immunize an animal. During the succeeding period of from two (2) weeks to twenty (20) weeks an antibody to the antigen is formed in the blood of the immunized animal. It is clear that the invention hinges upon the success of the complexing association reaction of asbestos with the antigenic blood serum protein.

THE GENERAL INVENTION

In the preliminary step an antigenic serum protein in a buffered saline solution is mixed with chrysotile asbestos to form a reaction product or conjugate. The antigenic serum proteins are selected from the group consisting of albumin, alpha globulin, beta globulin, and fibrinogen. The antigen produced as the reaction product is then used to immunize an animal. After a sufficient period for development, usually from two (2) to twenty weeks, antibody globulins are removed and isolated from the animal.

In general a blood protein selected from the group consisting of albumin, alpha globulin, beta globulin, and fibrinogen are all well known in the medical arts and are commercially available.

It should be understood that the reaction of serum proteins with asbestos is not well understood and is probably not a chemical reaction in terms of the usual dictionary definitions. There is no breaking of chemical bonds. The applicant advances the following theory of reaction that probably amounts to the formation of an association of conjugate of the antigenic protein with a plurality of asbestos molecules. For example albumin has a number of different amino-acids that form a number of combining sites. In theory each of these aminoacid sites may combine with a molecule of asbestos. This combination that takes place at room temperature of 78° F. or preferably from 50° to 90° F. is loosely referred to as a reaction producing a reaction product. The aminoacids which form the combining site appear to be so arranged as to present a surface pattern which is complementary to the asbestos or to the particular part of the surface of the asbestos molecule concerned. It is possible that the forces which bind the protein and the asbestos together are partly due to the presence of oppositely charged groups in close contact, and partly to the van der Waals forces—weak forces which act between molecules independently of charge, and whose strength falls off very sharply (approximately as the 6th power) as the distance between them increases. The strength of such forces in holding the protein and the asbestos together in the association or conjugated product will depend greatly upon the goodness of fit and nearness with which they can approach one another.

The pH of the reaction medium at which the van der Waals process are maximum is in the range of 6.8 to 7.2.

In the examples, to be set forth in detail hereinafter albumin has the empirical formula of ($C_{72}H_{112}N_{18}O_{22}S$) is reacted chrysotile asbestos of the general formula $Mg_3Si_2O_5(OH)_4$.

In theory one mole of protein (albumin) may associate or conjugate with from 4 to 100 moles of asbestos, depending upon the number of active sites present on the protein. In one or more of the examples 1 milligram of bovine serum albumin in a buffered saline solution is reacted with 50 milligrams of chrysotile asbestos.

It is advantageous to always have an excess of asbestos in the reaction medium to assure that not all of the asbestos is occluded by protein. In one preferred embodiment the ratio of antibody to asbestos varies from about 1 to 10 to 1 to 200 by weight. In another preferred embodiment the antibody toward asbestos in the saline solution may vary from about 0.2 milligrams per millimeter to about 5 milligrams per milliliters (mg/ml).

The ratios of milligrams of protein to asbestos present in the reaction medium may vary from about 1 to 10 to 1 to 200. This range of ratios will usually assure an excess of asbestos.

The antigenic serum protein is suspended in a buffered dilute saline solution before the asbestos is introduced. A buffered phosphate saline solution is one that is preferred. Many other buffered saline solutions are known to those skilled in the medical art. All such known buffered solutions are generally equivalent and are commercially available.

The concentration of antigenic serum protein in the buffered saline solution will vary between about 0.02 milligrams per ml to about 5 milligrams per milliter (mg/ml).

In general the buffered saline solution containing bovine serum albumin and chrysotile asbestos is stirred or moderately agitated so as to promote the rapid progression of the reaction The conjugate may then be separated by antifugation and resuspended in saline buffered solution.

Where albumin is the protein selected for reaction it should be understood that albumin taken or isolated from humans, cows, horses, sheep, goats, guinea pigs or swine albumins may be used.

In the next step in the process of producing the antibody toward asbestos the reaction product (antigen) of the asbestos with the protein is used to immunize a laboratory animal.

Although any of the known laboratory animals may be used to produce the antibody to asbestos the preferred animal is the rabbit.

The preferred combination, that gives the best results are where antigenic serum protein is contributed by a member of the cow family, hereinafter referred to as bovine serum albumin (BSA) and the laboratory animal producing the antibody toward asbestos is the rabbit.

The animal that produces the antibody should be of a different species than the animal that contributes the antigenic serum protein, i.e., cow contributes the albumin and the rabbit is the laboratory animal.

That is to say that a rabbit should not contribute the antigenic serum protein and then the same rabbit or another rabbit be immunized to produce the antibody. Any other combination of animals should give satisfactory results but the BSA-asbestos combined with rabbit production of antibody is preferred.

DESCRIPTION OF THE PREFERRED EMBODIMENTS

SPECIFIC PROCEDURES

Example 1

Preparation of Antigen

The preparation of BSA-coated asbestos was carried out by adding approximately 1 mg of BSA in 5 ml of saline phosphate buffer to 50 mg of chrysotile in a 12 ml centrifuge cone and thoroughly stirring the mixture. An interesting consequence of coating the asbestos was observed: namely, that the asbestos became much more highly dispersed and settled much more slowly from solution than was observed when asbestos was stirred in ordinary water. This is undoubtedly a direct consequence of the fact that protein molecules will not bind to each other (with the exception of hapten or antigen and antibody molecules). This observation proved to be important later in the study. The reaction product is called the antigen.

Preparation of Antibody

Two such preparations were made, one of which was lyophilized. Both antigen preparations were sent to Miles Laboratories of Elkhart, Indiana for injection and boosting of four rabbits per preparation and with a final blood sampling scheduled for 10 weeks after the initial boost.

Each of the four rabbits was injected with 1 ml of the antigen reaction product produced in step 1.

Subsequently, after ten (10) weeks the globulins were separated from the rabbit blood by ammonium sulphate precipitation, lyophilized, and shipped to the inventor.

The globulins from rabbits injected with non-lyophilized asbestos-albumin antigen will be referred to as NAAG, the globulins from rabbits injected with lyophilized astestos-albumin antigen will be referred to as LAAG, and the globulins from uninjected rabbits (rabbit control globulin) will be referred to as NRG.

Preparation of Labeled Globulins

Fluorescein isothiocyanate (4.9 mg) was dissolved in 0.35 ml of pH9 carbonate buffer, and 0.35 ml of the solution was added to each of three solutions of globulin: (1) 89.7 mg of NRG in 3 ml of saline, (2) 149.5 mg of NAAG in 4 ml of saline, and (3) 94.3 mg of LAAG in 3 ml of saline. The solutions were stirred and allowed to stand for 24 hours at 5° C. in a refrigerator. The labeled globulin was separated from unreacted fluorescein isothiocyanate in 1.5 ml of each solution by passing the 1.5 ml aliquots through a Sephadex G-25 column using saline phosphate solution as the eluant. Each separated labelled globulin fraction was divided into 3 portions in serum bottles and frozen.

The same procedure was used to label BSA with fluorescein. To 20 ml of a saline solution of BSA (4.73 mg BSA/ml) was added 1.5 ml of carbonate buffer (pH 9.3) containing 0.5 mg of fluorescein and isothiocyanate. After three hours of incubation a 2 ml aliquot was loaded on a Sephadex G-25 column and the labeled BSA was eluted away from unreacted fluor with neutral saline phosphate solution.

Four series of experiments were carried out. In the first series separate 1 mg of aliquots of chrysotile were incubated for one hour with 0.75 ml of 0.3 percent saline solutions of one of the proteins-BSA, NRG, NAAG, and LAAG-at 0.3 percent concentration. The globulins from the rabbits injected with non-lyophilized antigen are designated NAAG, and globulins from rabbits injected with lyophilized antigen are designated LAAG. Normal rabbit globulins were acquired from Miles Laboratories for experimental control, and are designated NRG. All globulin fractions were determined by electrophoresis to be free of albumin. The solutions were agitated in the beginning of the incubation and the degrees of settling of the asbestos at the end of the hour were compared. This experiment was also carried out with talc as the substrate.

In the second series of experiments 1.7 mg of asbestos in each of three tubes was incubated for one hour with 1 ml of 4.73 mg of BSA per ml of saline solution. The solution was centrifuged, and the asbestos was washed three times with saline solution followed by centrifugation each time. The washed asbestos was then incubated with NRG-F in one tube, NAAG-F in another tube, and LAAG-F in the third tube for 1.75 hours. In each case the concentration of labeled protein was 2 mg per ml. The asbestos was centrifuged and washed twice with saline, and examined for binding of fluorescein labeled reagent by irradiation with ultra-violet radiation (360 nm) in the dark.

In the third series of experiments separate 1 mg portions of asbestos were incubated for 10 minutes with 1 ml of saline solution containing one of the globulins, NRG-F, NAAG-F, or LAAG-F at 2 mg per ml, after which the asbestos was triple rinsed and examined under 360 nm radiation.

In the fourth series of experiments each of three 1.7 mg portions of asbestos was incubated with one ml of a saline containing a different globulin (NRG, LAAG, or NAAG) at 2.4 mg per ml for one hour. After incubation, the asbestos was centrifuged and washed twice with fresh saline solution. Each portion was mixed with 1.2 ml of saline, and 1 mg of BSA-F in 0.3 ml of saline was added to each mixture. After 1.75 hours of incubation all three tubes were centrifuged and the asbestos was washed with fresh saline solution. The asbestos was then examined for binding of fluorescein-labeled reagent as in the previous experiments.

RESULTS

The results of the four series of experiments are given in Tables 1, 2, 3, and 4.

TABLE 1

| | First Series of Experiments | |
|---|---|---|
| Reagent With Which Asbestos or Talc Was Incubated | Clarity of Supernate Over Asbestos After Setting for One Hour | Clarity of Supernate Over Talc After Setting for One Hour |
| BSA | Cloudy* | Cloudy |
| NAAG | Cloudy* | Clear |
| LAAG | Cloudy* | Clear |
| NRG | Clear | Clear |

These supernates were about equally cloudy

TABLE 2

Second Series of Experiments

| Reagent with Which BSA-Coated Asbestos was Incubator | Fluorescein Fluorescence (510 nm) from Asbestos After Rinsing |
|---|---|
| NRG-F | None |
| NAAG-F | Strong |
| LAAG-F | Strong |

TABLE 3

Third Series of Experiments

| Reagent With Which Asbestos was Incubated | Fluorescein Fluorescence (510 nm) from Asbestos After Rinsing |
|---|---|
| NRG-F | Moderate |
| NAAG-F | Strong |
| LAAG-F | Strong |

TABLE 4

Fourth Series of Experiments

| Reagent With Which Asbestos Was First Incubated | Fluorescein Fluorescence (510 nm) from Asbestos After Incubating With BSA-F and Rinsing |
|---|---|
| NRG | Strong |
| NAAG | None |
| LAAG | None |

The preliminary tests mentioned in the introduction, which indicated binding of BSA to chrysotile, were supported by the observation during preparation of the immunogen that chrysotile becomes highly dispersed and settles more slowly when incubated with a saline solution of BSA than when incubated with saline solution only. It is apparent that the protein coating interferes with the tendency of chrysotile fibrils to sediment.

The dispersal test was the basis of the first experiments with rabbit globulins, and the results indicate that the globulins from the immunized rabbits adhered to the asbestos, while the control globulins did not appreciably adhere. This indicates that the immunized rabbit globulins contained antibody toward asbestos. The control experiments with talc showed a decreased sedimentation rate with albumin but no change in the presence of any of the globulins; this result implies that the globulins were relatively free of albumin.

The results from the second series of experiments show that control globulins did not appreciably combine with a BSA-treated asbestos while the experimental globulins reacted strongly. This implies that the experimental globulins contain antibody toward BSA.

The results from the third series of experiments with fluorescein-labeled globulins show that there is some uptake by asbestos of fluorescein-labeled normal, as well as experimental, globulins. However, it appears that uptake of the later is greater.

The results from the fourth series of experiments support the foregoing interpretations. BSA-F adhered only to the chrysotile previously incubated with control globulins, NRG, but not to the chrysotile incubated with the experimental globulins. Since it had been previously shown in the first experiments that NRG did not appreciably adhere to chrysotile while BSA adhered strongly, this result was to be expected. On the other hand, the fact that BSA-F did not adhere to chrysotile that had previously been incubated with experimental globulins implies both: (1) that the asbestos had been coated with antibody from the experimental globulins, and (2) that any anti-BSA present was not absorbed on the fibers to subsequently take up BSA-F.

The results of the experiments give substantial evidence that the original BSA-asbestos immunogen induced the generation of antibody to asbestos, as well as to BSA, when injected into rabbits. In addition to providing an immunochemical reagent for the determination of chrysotile, this physiological response may be of relevance in the study of the materials carcinogenicity.

The reaction product of asbestos with an antigenic protein has utility as an intermediate and as an antigenic reagent. It is also apparent that it is this antigenic reagent is capable of causing the laboratory animal to produce antibody. This antibody toward asbestos is a reagent for detecting asbestos. The antibody is chemically and morphologically sensitive to asbestos.

It is clear that the foregoing disclosure and the examples illustrate methods for detecting asbestos in the air or in a liquid sample, whether in a solution or suspended in a liquid, like water.

In one method for detecting asbestos in a sample taken from the air, the sample can be simply agitated with the antibody toward asbestos, as illustrated in the examples. If there is asbestos present in the sample then a reaction will take place, producing a visible suspension. This method can be made quantative by making a comparison chart, indicating heavier suspension have a higher concentrations of asbestos in the sample.

When the asbestos sample is suspended in water or other diluent or is in solution the fluorescein labeling techniques may be used. In this method the antibody toward asbestos is (a) labeled with fluorescein (b) the labeled antibody is added to the sample containing asbestos. If there is any asbestos present it will react with the antibody forming a suspension (c) the suspension should be filtered and then (d) the filtered particles can be examined with an ultra violet light.

If it is desirable to quantatively determine the presence of asbestos particles the fluorescent particles present on the filter can be counted.

What is claimed as new and desired to be secured by Letters Patent of the United States is:

1. A method for the production of antibodies to asbestos comprising the steps of (a) reacting asbestos with an antigenic serum protein (b) recovering the antigenic reaction product (c) immunizing an animal with said antigenic reaction product (d) allowing a sufficient period of time for the production in the animal of an antibody to asbestos and (e) recovering said antibody from the animal.

2. The method of claim 1 wherein the antigenic serum protein is selected from the group consisting of albumin, alpha globulin beta globulin, and fibrinogen.

3. The method of claim 2 wherein an animal albumin is reacted with crysotile asbestos.

4. The method of claim 2 wherein the antigenic serum protein is first dissolved in a buffered saline solution.

5. The method of claim 4 wherein the antigenic serum protein is disolved in a buffered saline solution at room temperature.

6. The method of claim 1 wherein the period of time for development of the antibody is from about two weeks to about twenty weeks.

7. The method of claim 1 wherein bovine serum albumin is reacted with asbestos.

8. The method of claim 7 wherein the ratio of albumin to asbestos is in the range of 1 to 10 to 1 to 200 based on weight.

9. The method of claim 1 wherein bovine serum albumin is reacted with chrysotile asbestos and the reaction product is used to immunize a rabbit.

10. A method of producing an antigenic complex comprising the steps of (1) dissolving a serum protein in a buffered saline solution (2) reacting the saline solution containing the serum protein with chrysotile asbestos and recovering the resulting product.

11. The method of claim 10 wherein the buffered saline solution has a pH in the range of 6.8 to 7.2.

12. The method of claim 11 wherein the concentration of serum protein is present in the range from 0.02 mg per ml to about 5 mg per ml in the buffered saline solution.

13. The method of claim 11 wherein the concentration of asbestos is present in the range of from about 0.01 mg per ml to about 100 milligrams per ml.

14. The method of claim 11 wherein the ratio of protein to asbestos in the reaction medium varies from about 1:10 to 1 to 200.

15. The method of producing an antibody toward asbestos comprising the steps of (a) mixing a buffered saline solution containing an antigenic serum protein with a sufficient quantity of asbestos to combine with all active sites on each asbestos molecule so as to produce reaction product (b) recovering the said reaction product of step (a)

(c) immunizing a laboratory animal with the reaction product of step (a)

(d) allowing an antibody to form in the blood of the laboratory animal for a period of at least two weeks and (e) recovering the blood of the laboratory animal and isolating an antibody toward asbestos.

16. A method of detecting asbestos comprising the steps of mixing a sample of material containing asbestos with an antibody toward asbestos, forming a suspension of reaction product of antibody and asbestos and visually observing the density of the suspension.

17. A method of detecting the presence of asbestos in a sample solution comprising, the steps of (a) labeling an antibody toward asbestos with fluorescein (b) adding the labeled antibody to the sample solution (c) filtering the solution (d) examining the filter with a ultra violet light (e) counting the fluorescent particles present on the filter.

18. The method of claim 16 wherein the ratio of antibody to asbestos varies from about 1 to 10 to 1 to 200 by weight.

19. The method of claim 18 wherein the antibody to asbestos is dissolved in a buffered saline solution.

20. The method of claim 19 wherein the of antibody toward asbestos in the buffered saline solution varied from about 0.2 milligrams per ml to about 5 milligrams per ml.

* * * * *